United States Patent [19]

Rattner et al.

[11] Patent Number: 4,984,565

[45] Date of Patent: Jan. 15, 1991

[54] EXTRACORPOREAL LITHOTRIPTOR WITH X-RAY LOCATING SYSTEM

[75] Inventors: Manfred Rattner, Grossenseebach; Franz Plisek, Erlangen, both of Fed. Rep. of Germany

[73] Assignee: Siemens Aktiengesellschaft, Berlin and Munich, Fed. Rep. of Germany

[21] Appl. No.: 426,967

[22] Filed: Oct. 26, 1989

[30] Foreign Application Priority Data

Dec. 9, 1988 [EP] European Pat. Off. ........ 88120646.0

[51] Int. Cl.$^5$ .............................................. A61B 17/22
[52] U.S. Cl. .............................................. 128/24 OEL
[58] Field of Search ........ 128/24 AA, 24 EL, 660.03; 606/127, 128; 378/99, 147, 154

[56] References Cited

U.S. PATENT DOCUMENTS

| | | | |
|---|---|---|---|
| 4,610,249 | 9/1986 | Makofski et al. | 128/24 EL |
| 4,688,242 | 8/1987 | Ema | 378/154 |
| 4,705,026 | 11/1987 | Chaussy et al. | 128/24 EL |
| 4,771,787 | 9/1988 | Wurster et al. | |
| 4,796,613 | 1/1989 | Heumann et al. | |
| 4,811,725 | 3/1989 | Grasser | |
| 4,877,017 | 10/1989 | Hahn et al. | 128/24 EL |

FOREIGN PATENT DOCUMENTS 0286170 10/1988 European Pat. Off. ....... 128/24 EL

Primary Examiner—Lee S. Cohen
Assistant Examiner—John D. Zele
Attorney, Agent, or Firm—Hill, Van Santen, Steadman & Simpson

[57] ABSTRACT

An extracorporeal lithotriptor has a shock wave head which includes a shock wave generator which generates shock waves to disintegrate calculi in situ, and components for coupling the generated shock wave to the patient. The lithotriptor also includes an x-ray system for locating a calculus to be disintegrated. The x-radiator for the x-ray system and the shock wave head are arranged relative to each other so that a central x-ray of the x-ray system proceeds substantially centrally through the shock wave head. The shock wave head can be arranged either at the housing of the primary radiation diaphragm for the x-ray system, or in front of the input luminescent screen of an x-ray image intensifier. The shock wave head has a central region which is penetrated by x-rays and which does not attenuate the x-rays.

5 Claims, 1 Drawing Sheet

EXTRACORPOREAL LITHOTRIPTOR WITH X-RAY LOCATING SYSTEM

BACKGROUND OF THE INVENTION

1. Field of the Invention

The present invention is directed to a lithotriptor having an x-ray system for locating calculi to be disintegrated, and a shock wave head for generating shock waves and coupling the shock waves to a patient to achieve disintegration of the calculi.

2. Description of the Prior Art

Lithotriptor systems are known in the art which are provided with two x-ray systems, each having an x-ray source and an x-ray detector, such as an x-ray image intensifier, with a video chain connected thereto. The patient is transirradiated with x-rays from two directions, so that it is possible to locate a calculus to be disintegrated. Two shock wave applicators are adjustably mounted so that one of the shock wave applicators can be moved laterally to the patient for treatment. A central axis in the direction of shock wave propagation, and the central rays two x-ray systems, intersect in an isocenter in which the calculus to be treated is located. Because the plane which is defined by the two central rays of the acoustic lobes of the respective shock wave applicators is perpendicular to the plane defined by the two central rays of the x-ray systems, the lateral space requirement for the overall system is relative large.

SUMMARY OF THE INVENTION

It is an object of the present invention to provide a lithotriptor of the type described above having a more compact structure than conventional systems.

The above object is achieved in accordance with the principles of the present invention in a lithotriptor having a shock wave head arranged relative to an x-ray source of an x-ray locating system so that a central ray from the x-ray source proceeds substantially centrally through the shock wave head. The shock wave head can thus be disposed following the x-radiator in the direction of radiation propagation. Lateral space is thus not required beneath the patient support table, as in conventional systems.

The shock wave head has a central region through which the x-rays propagate without attenuation. This may be formed, for example, by a hollow, cylindrical air-filled volume within the shock wave head, which is penetrated by the x-radiation. This provides especially good imaging and permits simple observation of the region of the patient which is subjected to the action of the shock waves during treatment. The shock wave head may be arranged at the primary radiation diaphragm of the x-ray system, or can be arranged preceding the radiation detector for the x-ray system, for example preceding an x-ray image intensifier.

DESCRIPTION OF THE PREFERRED EMBODIMENTS

Figure 1:
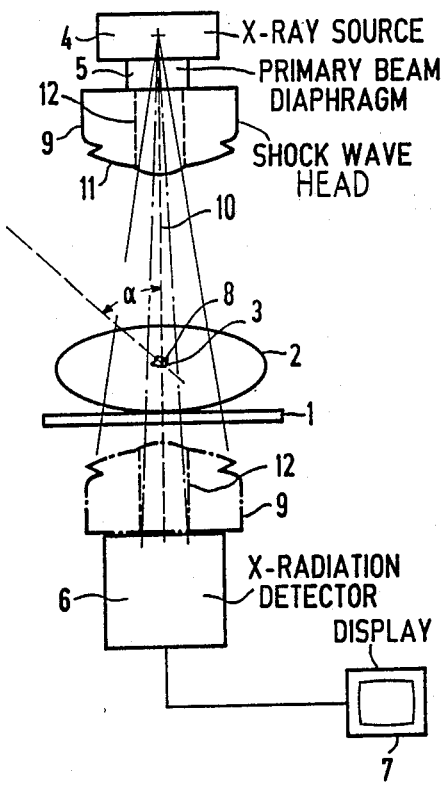
FIG. 1 is a schematic block diagram of a lithotriptor with an x-ray locating system constructed in accordance with the principles of the present invention.

A lithotriptor constructed in accordance with the principles of the present invention is shown in FIG. 1. The lithotriptor includes a patient support 1, on which a patient 2 having a calculus 3 lies. The lithotriptor includes an x-ray system for locating the position of the calculus 3 within the patient 2. The x-ray locating system includes an x-ray source 4 having a primary diaphragm 5, an x-ray detector 6, such as an x-ray image intensifier, and a video system including a display 7 on which an image corresponding to the x-ray image can be seen. The x-ray source 4, the primary beam diaphragm 5 and the radiation detector 6 can be pivoted around an axis 8 by an angle $\alpha$, so that transirradiation of the patient 2 from different directions can be undertaken, so that three-dimensional information about the position of the calculus 3 is obtained. The axis 8 preferably coincides with the calculus 3. The patient support 1 is adjustable in a known manner to achieve such coincidence.

After locating the position of the calculus 3, treatment in the form of disintegrating the calculus 3 takes place. For this purpose, the lithotriptor includes a shock wave head 9, which in the embodiment of FIG. 1 is shown mounted to and following the primary radiation diaphragm 5 in the direction of x-radiation propagation. The shockwave head 9 thus pivots around the axis 8 with the x-ray source 4, the radiation diaphragm 5 and the radiation detector 6. The shock wave head 9 emits shock waves, focussed to a focal region, with the shock wave head 9 and the patient 2 being relatively adjusted so that the focal region coincides with the calculus 3. For this purpose, the shock wave head 9 can be mounted so as to be adjustable in the direction of a central ray 10 of the x-ray source 4. Such adjustment can ensue individually, or in combination with the x-ray source 4. The side of the shock wave head 9 from which the shock waves exit is covered by a flexible sack 11, which is placed against the surface of the patient 2 for acoustic coupling.

As stated above, the shock wave head 9 is arranged relative to the x-ray system so that the central ray 10 of the x-ray system (i.e., the central ray 10 from the x-ray source 4) proceeds substantially centrally through the shock wave head 9. The shock wave head 9 has a central, hollow, cylindrical volume 12 which is penetrated by the x-radiation, and in which the x-radiation is not attenuated. The volume 12 is air-filled. The cylindrical wall limits the volume of the shock wave head 9 filled with coupling fluid, as is shown in greater detail in FIG. 2.

In the lithotriptor shown in FIG. 1, the central ray 10 of the x-ray system coincides with a central axis of the shockwaves emitted by the shock wave head 9. Locating of the calculus ensues by pivoting the x-ray system. It is also possible to provide a second x-ray system, which has a central ray defining the angle $\alpha$ together with the central ray 10, in which case the x-ray system shown in FIG. 1, (i.e., the x-ray source 4, the diaphragm 5 and the radiation detector 6) can be stationary. It is also possible to construct the x-ray source 4 for the production of the x-ray stereo images, by providing two foci from which x-rays propagate in alternation, so that the two central rays respectively proceeding from the two foci define a small angle relative to each other. In this case, the volume 12 must be dimensioned so that passage of both x-ray beams without attenuation ensues, so that both x-ray beams fully penetrate the patient 2.

A further possible placement location of the shock wave head 9 is shown in dot-dash lines in FIG. 1. The shock wave head 9 can alternatively be placed in front of the x-ray detector 6. If the x-ray detector 6 is an x-ray image intensifier, the shock wave head 9 will be placed immediately preceding the input screen of the x-ray image intensifier, in the direction of x-ray propagation. Again, the x-ray beam useable for imaging is defined by the dimensions of the volume 12.

Figure 2:
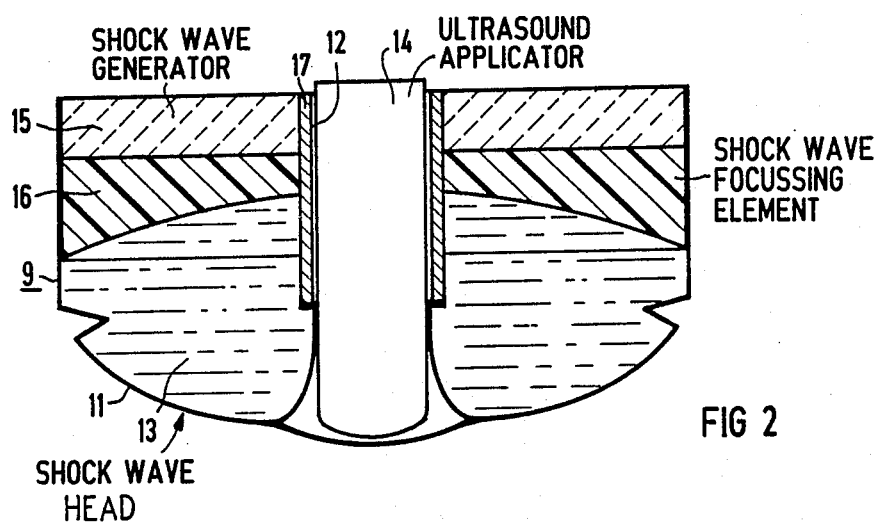
FIG. 2 is a side sectional view of a shock wave head for use in the lithotriptor of FIG. 1.

A shock wave head suitable for use in the lithotriptor of FIG. 1 is shown in FIG. 2 in section. The shock wave head 9 includes a shock wave generator 15, which may be a piezo-ceramic or an electrodynamic shock wave generator, followed by a shock wave focussing element 16. The shock wave focussing element 16 may be an acoustic lens, and may be adjustable for varying the position of the focal region. The exit face of the shock wave focussing element 16 and the flexible sack 11 define a closed volume 13, which is filled with coupling fluid. The volume 12, through which x-radiation passes unattenuated, is defined by a rigid cylindrical wall 17. If desired, an ultrasound applicator 14 which is part of an ultrasound locating system may be inserted in the space 12 in an axial direction. The ultrasound applicator 14 can be removed from the volume 12 when the x-ray locating system is operated. When the ultrasound applicator 14 is removed, the volume defined by the cylindrical wall 13 will be filled only with air, so that x-rays pass therethrough unattenuated.

Although modifications and changes may be suggested by those skilled in the art, it is the intention of the inventors to embody within the patent warranted hereon all changes and modifications as reasonably and properly come within the scope of their contribution to the art.

We claim as our invention:

1. An extracorporeal lithotriptor comprising:
   an x-ray locating means adapted for locating a calculus in a patient, said x-ray locating means including means for generating an x-ray beam propagating in a propagation direction and having a central ray; and
   a shockwave head including means for generating shockwaves and means adapted for coupling said shockwaves to said patient for in situ disintegration of said calculus, said shockwave head being disposed in said x-ray beam so that said central ray of said x-ray locating means proceeds substantially centrally through said shockwave head.

2. A lithotriptor as claimed in claim 1, wherein said shockwaves generated by said means for generating shockwaves have an acoustic propagation axis, and wherein said shockwave head is disposed relative to said x-ray locating means so that said central ray of said x-ray beam and said acoustic propagation axis coincide.

3. A lithotriptor as claimed in claim 2, wherein said shockwave head has a central region through which said x-ray beam proceeds substantially unattenuated.

4. A lithotriptor as claimed in claim 1, wherein said x-ray locating means includes a primary radiation diaphragm, and wherein said shockwave head is disposed immediately following said primary radiation diaphragm in said propagation direction of said x-ray beam.

5. A lithotriptor as claimed in claim 1, wherein said x-ray locating means includes a radiation detector, and wherein said shockwave head is disposed immediately preceding said radiation detector in said propagation direction of said x-ray beam.

* * * * *